US011877802B2

(12) United States Patent
Lavoritano et al.

(10) Patent No.: US 11,877,802 B2
(45) Date of Patent: Jan. 23, 2024

(54) PERSPECTIVE FRAME MATCHING PROCESS FOR DEFORMED FIXATION RINGS

(71) Applicant: Depuy Synthes Products, Inc., Raynham, MA (US)

(72) Inventors: Scott Lavoritano, West Chester, PA (US); Michael Wahl, West Chester, PA (US); Bernd Gutmann, Hassloch (DE); Vaughn Charlton, III, Ladenberg, PA (US); Albert Montello, Berwyn, PA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 421 days.

(21) Appl. No.: 17/138,461

(22) Filed: Dec. 30, 2020

(65) Prior Publication Data
US 2022/0202492 A1   Jun. 30, 2022

(51) Int. Cl.
A61B 34/10 (2016.01)
A61B 17/62 (2006.01)
A61B 34/00 (2016.01)

(52) U.S. Cl.
CPC .............. *A61B 34/10* (2016.02); *A61B 17/62* (2013.01); *A61B 34/25* (2016.02)

(58) Field of Classification Search
CPC .... A61B 34/10–2034/108; A61B 17/60–17/66
See application file for complete search history.

(56) References Cited

U.S. PATENT DOCUMENTS 5,728,095 A    3/1998  Taylor et al.
6,587,802 B1   7/2003  Schroder et al.
(Continued)

FOREIGN PATENT DOCUMENTS

EP     2134515      12/2009
WO   WO2017139517   8/2017

OTHER PUBLICATIONS

International Search Report for PCT/IB2021/061960 dated Mar. 22, 2022.

*Primary Examiner* — Julianna N Harvey
(74) *Attorney, Agent, or Firm* — Kramer & Amado, P.C.

(57) ABSTRACT

A computer-implemented method for producing a treatment plan to control manipulation of a fixation apparatus including a first element and a second ring and struts to correct an anatomical structure deformity of first and second anatomical structure segments, including: receiving, using one or more graphical user interfaces of a computing system, configuration information associated with the fixation apparatus, the configuration information comprising one or more geometric characteristics of one or more elements of the fixation apparatus and ring deformation information; receiving, by the computing system, images of the fixation apparatus and the first and the second anatomical structure segments attached thereto; determining, by the computing system, based on the configuration information and the received images, positions and orientations of the first and the second anatomical structure segments in three-dimensional space relative to the fixation apparatus; determining the hole locations of the first element based upon the deformation information; determining, by the computing system, manipulations to the fixation apparatus for correction of the anatomical structure deformity, the manipulations comprising adjustments to the struts based upon the determined hole location of the first element; and providing, by the computing system, to one or more users, indications of the manipulations to the fixation apparatus.

22 Claims, 5 Drawing Sheets

(56) References Cited

U.S. PATENT DOCUMENTS

| | | |
|---|---|---|
| 6,701,174 B1 | 3/2004 | Krause et al. |
| 7,837,621 B2 | 11/2010 | Krause et al. |
| 8,296,094 B2 | 10/2012 | Harrison et al. |
| 8,419,732 B2 | 4/2013 | Mullaney |
| 8,654,150 B2 | 2/2014 | Haskell |
| 8,952,986 B2 | 2/2015 | Haskell |
| 9,524,581 B2 | 12/2016 | Haskell |
| 9,642,649 B2 | 5/2017 | Nikonovas |
| 9,724,129 B2 | 8/2017 | Edelhauser et al. |
| 9,788,908 B1 | 10/2017 | Haskell |
| 9,895,167 B2 | 2/2018 | Edelhauser et al. |
| 10,010,346 B2 | 7/2018 | Edelhauser et al. |
| 10,082,384 B1 | 9/2018 | Singh |
| 10,154,884 B2 | 12/2018 | Kumar et al. |
| 10,213,261 B2 | 2/2019 | Haskell |
| 10,251,705 B2 | 4/2019 | Kumar et al. |
| 10,349,981 B2 | 7/2019 | Burgherr et al. |
| 10,603,112 B2 | 3/2020 | Kumar et al. |
| 10,610,304 B2 | 4/2020 | Haskell |
| 2003/0191466 A1 | 10/2003 | Austin et al. |
| 2004/0073211 A1 | 4/2004 | Austin et al. |
| 2007/0146371 A1 | 6/2007 | Dariush |
| 2010/0087819 A1 | 4/2010 | Mullaney |
| 2017/0303966 A1 | 10/2017 | Edelhauser et al. |
| 2018/0055569 A1* | 3/2018 | Wahl ................ G06T 7/70 |
| 2018/0168703 A1 | 6/2018 | Roman et al. |
| 2018/0256210 A1 | 9/2018 | Mullaney |
| 2019/0117314 A1 | 4/2019 | Haskell |
| 2020/0179054 A1 | 6/2020 | Haskell |

\* cited by examiner

PERSPECTIVE FRAME MATCHING PROCESS FOR DEFORMED FIXATION RINGS

TECHNICAL FIELD

Various exemplary embodiments disclosed herein relate generally to a perspective frame matching process for deformed fixation rings.

BACKGROUND

Techniques used to treat fractures and/or deformities of anatomical structures, such as bones, may include the use of external fixators, such as hexapods and other fixation frames, which are surgically mounted to anatomical structure segments on opposed sides of a fracture site. A pair of radiographic images is taken of the fixator and anatomical structure segments at the fracture site. Data from the images is then manipulated with orthogonal projection techniques to construct a three dimensional representation of the fixator and the anatomical structures segments that may be used in developing a treatment plan, which may for example comprise realigning the anatomical structure segments through adjustments to the fixator.

Existing techniques for controlling fixator manipulation may, however, involve a number of limitations that may introduce inefficiency, complication, and unreliability. For example, some conventional techniques may require radiographic images to be orthogonal with respect to each other and aligned with anatomical axes of the patient. As yet another example, some conventional techniques may require fixator struts to be mounted into only standard ring holes or may require a reference ring to be orthogonal with respect to an anatomical structure segment to which it is mounted. Additionally, some conventional techniques may be limited with respect to how treatment plans are generated, providing few, if any, options for generating plans based on different needs and characteristics of the patient. Furthermore, some conventional techniques may be limited with respect to feedback provided to users, such as providing few, if any, confirmations of values and calculations. These and other limitations may unnecessarily increase the cost and complexity of the manipulation process. Additionally, these limitations may also reduce the reliability of the treatment plan, possibly resulting in improper alignment of anatomical structures segments during the healing process, compromised union between the anatomical structure segments, necessitating additional rounds of radiographic imaging to facilitate alignment corrections, or even necessitating additional surgical procedures.

An improvement in techniques for orthopedic fixation control and manipulation, for example for correction of a deformity of an anatomical structure, such as a bone, have been developed. In particular, in some examples, a fixation apparatus may be attached to first and second anatomical structure segments. Images of the fixation apparatus and the attached anatomical structure segments may then be captured from different orientations with respect to the fixation apparatus.

In some examples, various manipulations to the fixation apparatus for correction of the anatomical structure deformity may be determined using one or more techniques. For example, in some cases, the manipulations to the fixation apparatus may be determined using a technique referred to hereinafter as Perspective Frame Matching (PFM). In the PFM technique, the images of the fixation apparatus and the attached anatomical structure segments need not necessarily be orthogonal (e.g., may be non-orthogonal) with respect to one another. In some examples of the PFM technique, configuration information associated with the fixation apparatus may be received, for example using one or more graphical user interfaces of the computing system. The received configuration information may include one or more geometric characteristics of one or more elements of the fixation apparatus, such as ring type, ring diameter, strut size, strut length, and other geometric characteristics. The captured images of the fixation apparatus and the attached anatomical structure segments may then be displayed, for example using one or more graphical user interfaces of a computing system. Upon displaying of the images, first image information may then be received, for example using the one or more graphical user interfaces of the computing system. The first image information may include indications of one or more locations, within the images, of at least part of one or more elements of the fixation apparatus. For example, the first image information may include indications of hinge locations, strut locations, and other fixation apparatus element locations within the images. Additionally, second image information may then be received, for example using the one or more graphical user interfaces of the computing system. The second image information may include indications of one or more locations, within the images, of at least part of the first and the second anatomical structure segments. For example, the second image information may include indications of reference points (e.g., end points) and center lines of the first and the second anatomical structure segments within the images. The configuration information, the first image information, and the second image information may then be used, for example, to determine positions and orientations of the first and the second anatomical structure segments in three-dimensional space. Manipulations to the fixation apparatus for correction of the anatomical structure deformity may then be determined, and indications of the determined manipulations may then be provided to one or more users. The manipulations to the fixation apparatus may include adjustments to the struts of the fixation apparatus, such as adjustments to the sizes and/or lengths of the struts.

As an alternative or in addition to the PFM technique, various other techniques may also be employed for determining manipulations to the fixation apparatus for correction of the anatomical structure deformity. For example, in some cases, a technique referred to hereinafter as the Standard technique may be employed, in which various deformity and mounting parameters may be measured, for example by a surgeon, and entered manually into software. In some examples, in order to ensure accuracy of calculations for the Standard technique, the images of the fixation apparatus and the attached anatomical structure segments may be required to be orthogonal with respect to one another.

As another example, in some cases, yet another technique, referred to hereinafter as the Acute Intentional Deformation (AID) technique, may be employed for determining manipulations to the fixation apparatus for correction of the anatomical structure deformity. In some examples, the AID technique may be advantageous for correction of deformities, such as broken bones or congenital bone deformities, in which a patient's anatomical structures and/or the fixation apparatus may be manipulated such that final strut positions correspond with the corrected anatomical structure. In some examples of the AID technique, a user may enter initial (corresponding to deformed anatomical structure) and final (corresponding to corrected anatomical structure) strut positions, and the manipulations to the fixation apparatus for correction of the anatomical structure deformity may be determined based, at least in part, on the initial and final strut positions.

SUMMARY

A summary of various exemplary embodiments is presented below. Some simplifications and omissions may be made in the following summary, which is intended to highlight and introduce some aspects of the various exemplary embodiments, but not to limit the scope of the invention. Detailed descriptions of an exemplary embodiment adequate to allow those of ordinary skill in the art to make and use the inventive concepts will follow in later sections.

Various embodiments relate to a computer-implemented method for producing a treatment plan to control manipulation of a fixation apparatus including a first element and a second element and struts to correct an anatomical structure deformity of an anatomical structure having first and second anatomical structure segments, including: receiving configuration information associated with the fixation apparatus, the configuration information comprising one or more geometric characteristics of one or more elements of the fixation apparatus and element deformation information; receiving, by the computing system, images of the fixation apparatus and the first and the second anatomical structure segments attached thereto; determining, by the computing system, based on the configuration information and the received images, positions and orientations of the first and the second anatomical structure segments in three-dimensional space relative to the fixation apparatus; determining the hole locations of the first element based upon the deformation information; determining, by the computing system, manipulations to the fixation apparatus for correction of the anatomical structure deformity, the manipulations comprising adjustments to the struts based upon the determined hole location of the first element; and providing, by the computing system, to one or more users, indications of the manipulations to the fixation apparatus.

Various embodiments are described, wherein the deformation information includes a number of wires used and a tension on the wires, and determining the hole locations of the first element based upon the deformation information includes using a lookup table to determine hole locations of the first element based upon the number of wires and the tension.

Various embodiments are described, wherein the deformation information includes a tension value for each of the number of wires.

Various embodiments are described, wherein the deformation information includes attachment hole location information for each of the number of wires and the wire fixation devices.

Various embodiments are described, wherein determining the hole locations of the first element based upon the deformation information includes using lookup table tension values and using interpolation to determine the hole locations.

Various embodiments are described, wherein the lookup table is generated using finite element analysis of the first element.

Various embodiments are described, wherein the deformation information includes a measurement of an element opening in the first element, and determining the hole locations of the first element based upon the deformation information includes using a lookup table to determine hole locations of the first element based upon the element opening measurement.

Various embodiments are described, wherein the lookup table is generated using finite element analysis of the first element.

Various embodiments are described, wherein determining the hole locations of the first element based upon the deformation information includes using lookup table element opening values and using interpolation to determine the hole locations.

Various embodiments are described, wherein the deformation information includes a measurement of an element opening in the first element, and determining the hole locations of the first element based upon the deformation information includes using a hole location equation to determine hole locations of the first element based upon the element opening measurement.

Various embodiments are described, wherein the hole location equation is generated using finite element analysis of the first element.

Various embodiments are described, wherein element opening measurement is determined using a physical measurement.

Various embodiments are described, wherein the physical measurement is determined using a dedicated measurement tool.

Various embodiments are described, wherein element opening measurement is determined using a digital measurement.

Various embodiments are described, further comprising detecting markers in the received images of the fixation apparatus and producing the digital measurement of the element opening based upon the detected markers.

Various embodiments are described, wherein the deformation information includes a measurement of strain from a strain gauge in the first element, and determining the hole locations of the first element based upon the deformation information includes using a lookup table to determine hole locations of the first element based upon the strain measurement.

Various embodiments are described, wherein the lookup table is generated using finite element analysis of the first element.

Various embodiments are described, wherein determining the hole locations of the first element based upon the deformation information includes using lookup table strain values and using interpolation to determine the hole locations.

Various embodiments are described, wherein the deformation information includes a measurement of strain from a first strain gauge in the first element, and determining the hole locations of the first element based upon the deformation information includes using a hole location equation to determine hole locations of the first element based upon the strain measurement.

Various embodiments are described, wherein the hole location equation is generated using finite element analysis of the first element.

Various embodiments are described, wherein the deformation information includes a measurement of a first strain from a first strain gauge and a second strain from a second strain gauge in the first element, and determining the hole locations of the first element based upon the deformation information based upon the first strain measurement and the second strain measurement.

Various embodiments are described, wherein the configuration information is received from one or more graphical user interfaces.

BRIEF DESCRIPTION OF THE DRAWINGS

In order to better understand various exemplary embodiments, reference is made to the accompanying drawings, wherein.

To facilitate understanding, identical reference numerals have been used to designate elements having substantially the same or similar structure and/or substantially the same or similar function.

DETAILED DESCRIPTION

The description and drawings illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various embodiments described herein are not necessarily mutually exclusive, as some embodiments may be combined with one or more other embodiments to form new embodiments.

Techniques and systems for correcting bone deformities and injuries have been developed using external fixation and manipulation. Such techniques and systems are described in U.S. patent application Ser. No. 15/247,333 filed Aug. 5, 2016, entitled ORTHOPEDIC FIXATION CONTROL AND MANIPULATION to Wahl et al. (Wahl), which is hereby incorporated by reference in its entirety for all purposes as if included herein. Wahl describes a system implemented in software that analyzes radiological images of an external fixation system attached to a patient. The external fixation system may include rings or open rings and adjustable struts connected between the rings. Wires and pins are used to secure the rings to the patients bones. The system analyzes the images of the external fixation system and surgeon provides input regarding the desired patient outcome. The software system then determines a treatment plan based upon the configuration of the external fixation system, surgeon inputs, and the desired outcome. The treatment may include daily adjustments of the strut lengths to achieve the desired outcome over time, which may be the correction of a deformity or an injury. The treatment plan may include daily strut length settings that the patient is able to adjust as required by the plan. At the completion of the plan the external fixation system has manipulated the patients bones into the desired locations relative to one another with supplemental bone growth helping the bones to heal in the proper final position.

Figure 1:
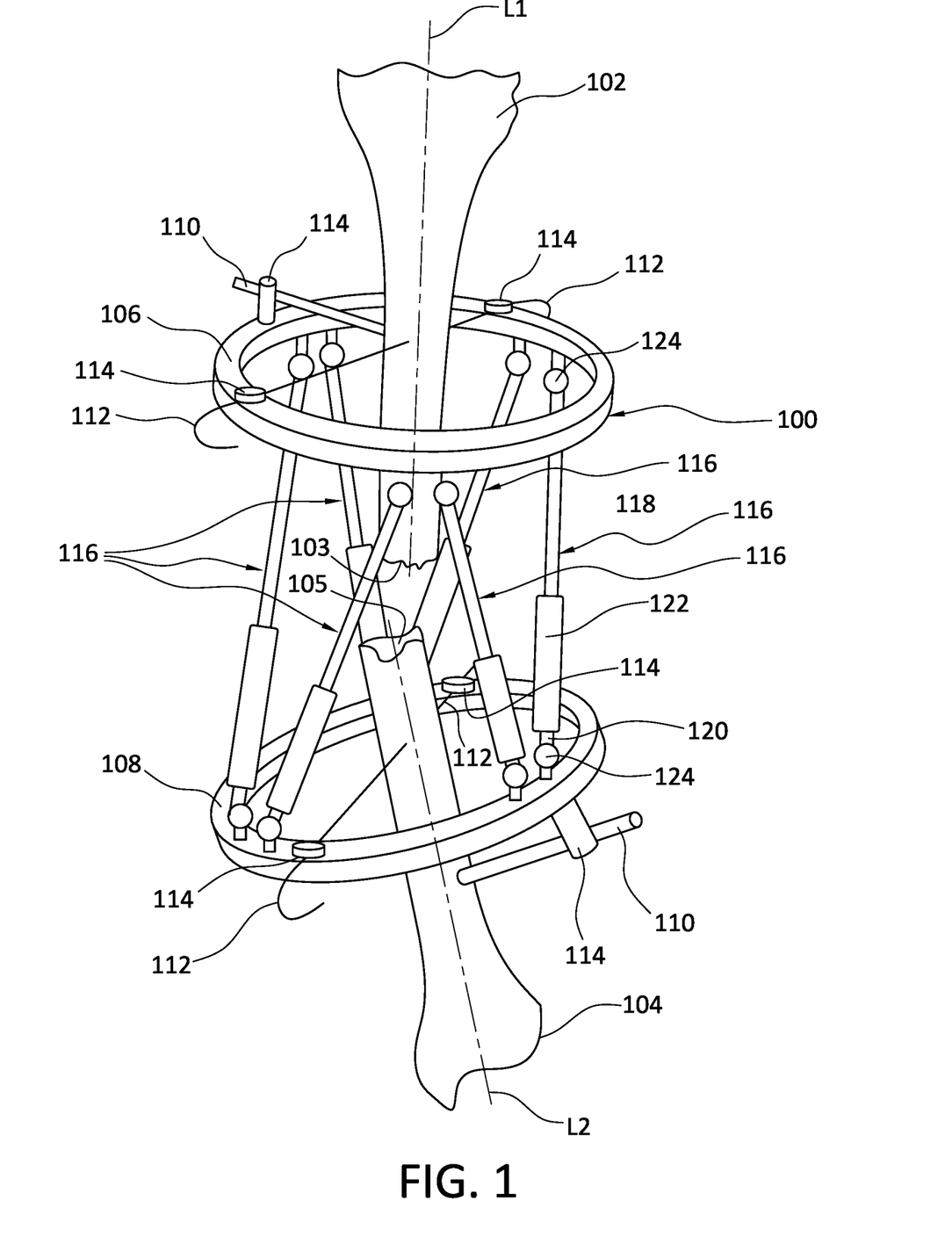
FIG. 1 illustrates an orthopedic fixator attached to two bone segments.

FIG. 1 illustrates an orthopedic fixator 100 attached to two bone segments. In FIG. 1, bodily tissues, for instance first and second anatomical structure segments 102, 104, may be aligned and/or oriented to promote union or other healing between the bodily tissues. Anatomical structures may include, for example, anatomical tissue and artificial anatomical implants. Anatomical tissue may include, for example, bone or other tissue in the body. The alignment and/or orientation of the bodily tissues may be achieved by connecting the bodily tissues to an adjustable fixation apparatus, such as orthopedic fixator 100. The orthopedic fixator 100 may comprise an external fixation apparatus that includes a plurality of discrete fixator members that remain external to the patient's body, but that are attached to respective discreet bodily tissues, for example with minimally invasive attachment members. A fixation apparatus may include, for example, a distraction osteogenesis ring system, a hexapod, or a Taylor spatial frame. By adjusting the spatial positioning of the fixator members with respect to each other, the respective bodily tissues attached thereto may be reoriented and/or otherwise brought into alignment with each other, for example to promote union between the bodily tissues during the healing process. The use of external orthopedic fixators in combination with the imagery analysis and positioning techniques described herein may be advantageous in applications where direct measurement and manipulation of the bodily tissues is not possible, where limited or minimally invasive access to the bodily tissues is desired, or the like. Some examples of orthopedic fixators and their use for correcting deformities of anatomical structure segments, as well as techniques for performing imagery analysis on the fixators and anatomical structure segments are described in U.S. patent application Ser. No. 13/111,180, entitled "ORTHOPEDIC FIXATION WITH IMAGERY ANALYSIS," filed on May 19, 2011, the entirety of which is hereby incorporated by reference for all purposes as if included herein.

The fixator members may be connected to each other via adjustment members with the adjustment members configured to facilitate the spatial repositioning of the fixator members with respect to each other. For example, in the illustrated embodiment, the orthopedic fixator 100 includes a pair of fixator members in the form of an upper fixator ring 106 and a lower fixator ring 108. The fixator rings 106, 108 may be constructed the same or differently. For instance, the fixator rings 106, 108 may have diameters that are the same or different. Similarly, the fixator rings 106, 108 may be constructed with varying cross sectional diameters, thicknesses, etc. It should be appreciated that the fixator members of the orthopedic fixator 100 are not limited to the illustrated upper and lower fixator rings 106, 108, and that the orthopedic fixator 100 may be alternatively constructed. For example, additional fixator rings may be provided and interconnected with the fixator ring 106 and/or 108. It should further be appreciated that the geometries of the fixator members are not limited to rings, and that at least one, such as all of the fixator members may be alternatively constructed using any other suitable geometry, such as partial or open rings (e.g., ⅝ or ¾ rings) or may be U-shaped members.

The first and second anatomical structure segments 102, 104 may be rigidly attached to the upper and lower fixator rings 106, 108, respectively, with attachment members that may be mounted to the fixator rings 106, 108. For example, in the illustrated embodiment, attachment members are provided in the form of attachment rods 110 and attachment wires 112.

The rods 110 and the wires 112 extend between proximal ends attached to mounting members 114 that are mounted to the fixator rings 106, 108, and opposed distal ends that are inserted into or otherwise secured to the anatomical structure segments 102, 104. The mounting members 114 may be removably mounted to the fixator rings 106, 108 at predefined points along the peripheries of the fixator rings 106, 108, for example by disposing them into threaded apertures defined by the fixator rings. With respect to each fixator ring 106, 108, the mounting members 114 may be mounted to the upper surface of the ring, the lower surface of the ring, or any combination thereof. It should be appreciated that the attachment members are not limited to the configuration of the illustrated embodiment. For example, any number of attachment members, such as the illustrated rods 110 and wires 112 and any others, may be used to secure the anatomical structure segments to respective fixator members as desired. It should further be appreciated that one or more of the attachment members, for instance the rods 110 and/or wires 112, may be alternatively configured to mount directly to the fixator rings 106, 108, without utilizing mounting members 114.

The upper and lower fixator rings 106, 108 may be connected to each other by at least one adjustment member or a plurality of adjustment members. At least one, of the adjustment members may be configured to allow the spatial positioning of the fixator rings with respect to each other to be adjusted. For example, in the illustrated embodiment, the upper and lower fixator rings 106, 108 are connected to each other with a plurality of adjustment members provided in the form of adjustable length struts 116. It should be appreciated that the construction of the orthopedic fixator 100 is not limited to the six struts 116 of the illustrated embodiment, and that more or fewer struts may be used as desired.

Each of the adjustable length struts 116 may comprise opposed upper and lower strut arms 118, 120. Each of the upper and lower strut arms 118, 120 have proximal ends disposed in a coupling member, or sleeve 122, and opposed distal ends that are coupled to universal joints 124 mounted to the upper and lower fixator rings 106, 108, respectively. The universal joints of the illustrated embodiment are disposed in pairs spaced evenly around the peripheries of the upper and lower fixator rings 106, 108, but may be alternatively placed in any other locations on the fixator rings as desired.

The proximal ends of the upper and lower strut arms 118, 120 of each strut 116 may have threads defined thereon that are configured to be received by complementary threads defined in the sleeve 122, such that when the proximal ends of the upper and lower strut arms 118, 120 of a strut 116 are received in a respective sleeve 122, rotation of the sleeve 122 causes the upper and lower strut arms 118, 120 to translate within the sleeve 122, thus causing the strut 116 to be elongated or shortened, depending on the direction of rotation. Thus, the length of each strut 116 may be independently adjusted with respect to the remaining struts. It should be appreciated that the adjustment members are not limited to the length adjustable struts 116 of the illustrated embodiment, and that the adjustment members may be alternatively constructed as desired, for example using one or more alternative geometries, alternative length adjustment mechanisms, and the like.

The adjustable length struts 116 and the universal joints 124 by which they are mounted to the upper and lower fixator rings 106, 108, allow the orthopedic fixator 100 to function much like a Stewart platform, and more specifically like a distraction osteogenesis ring system, a hexapod, or a Taylor spatial frame. That is, by making length adjustments to the struts 116, the spatial positioning of the upper and lower fixator rings 106, 108, and thus the anatomical structure segments 102, 104 may be altered. For example, in the illustrated embodiment the first anatomical structure segment 102 is attached to the upper fixator ring 106 and the second anatomical structure segment 104 is attached to the lower fixator ring 108. It should be appreciated that attachment of the first and second anatomical structure segments 102, 104 to the upper and lower fixator rings 106, 108 is not limited to the illustrated embodiment (e.g., where the central longitudinal axes L1, L2 of the first and second anatomical structure segments 102, 104 are substantially perpendicular to the respective planes of the upper and lower fixator rings 106, 108), and that a surgeon has complete flexibility in aligning the first and second anatomical structure segments 102, 104 within the upper and lower fixator rings 106, 108 when configuring the orthopedic fixator 100.

By varying the length of one or more of the struts 116, the upper and lower fixator rings 106, 108, and thus the anatomical structure segments 102 and 104 may be repositioned with respect to each other such that their respective longitudinal axes L1, L2 are substantially aligned with each other, and such that their respective fractured ends 103, 105 abut each other, so as to promote union during the healing process. It should be appreciated that adjustment of the struts 116 is not limited to the length adjustments as described herein, and that the struts 116 may be differently adjusted as desired. It should further be appreciated that adjusting the positions of the fixator members is not limited to adjusting the lengths of the length adjustable struts 116, and that the positioning of the fixator members with respect to each other may be alternatively adjusted, for example in accordance the type and/or number of adjustment members connected to the fixation apparatus.

Repositioning of the fixator members of an orthopedic fixation apparatus, such as orthopedic fixator 100, may be used to correct displacements of angulation, translation, rotation, or any combination thereof, within bodily tissues. A fixation apparatus, such as orthopedic fixator 100, utilized with the techniques described herein, may correct a plurality of such displacement defects individually or simultaneously. However, it should be appreciated that the fixation apparatus is not limited to the illustrated orthopedic fixator 100, and that the fixation apparatus may be alternatively constructed as desired. For example, the fixation apparatus may include additional fixation members, may include fixation members having alternative geometries, may include more or fewer adjustment members, may include alternatively constructed adjustment members, or any combination thereof.

Figure 2:
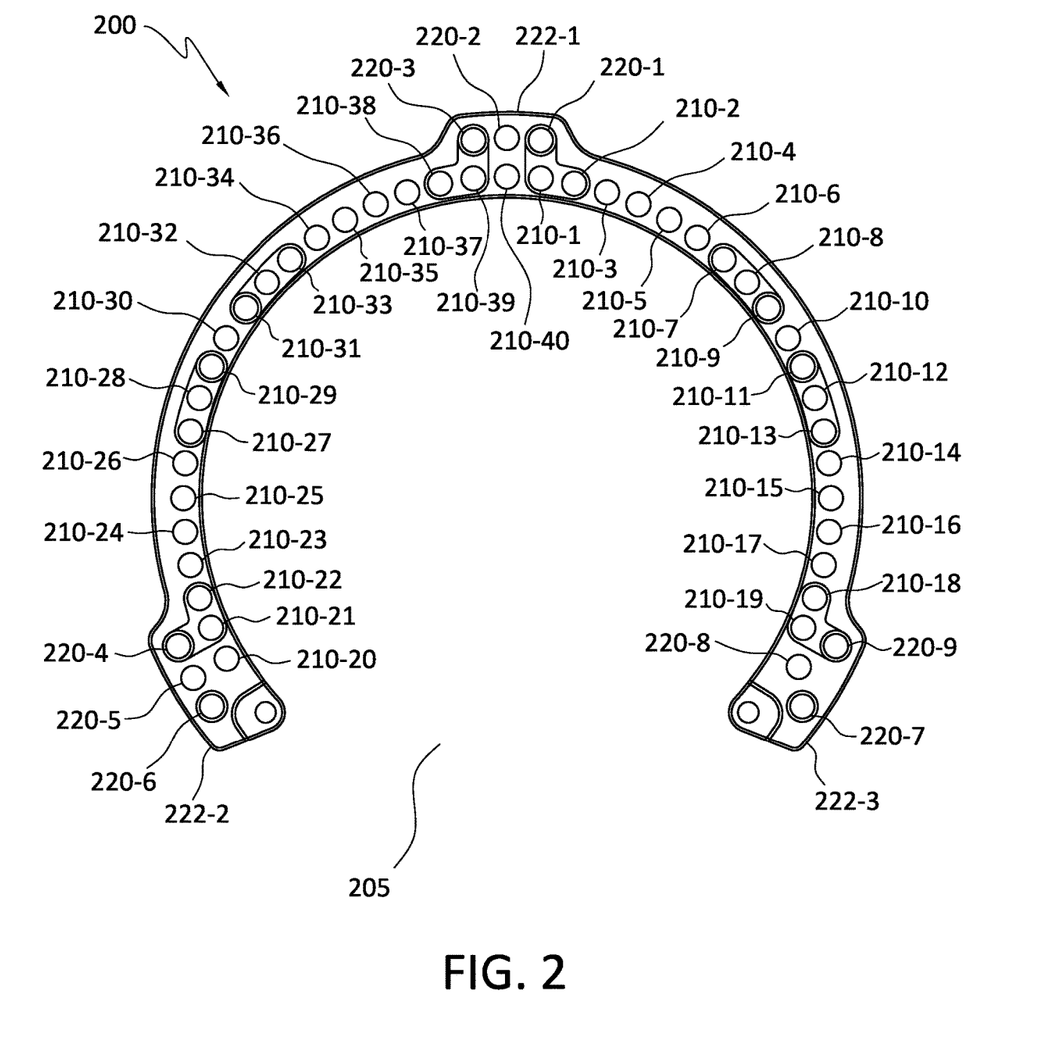
FIG. 2 illustrates an embodiment of ⅝ ring that may be used at part of the external fixator.

FIG. 2 illustrates an embodiment of ⅝ ring 200 that may be used at part of the external fixator. The ring 200 may be used to prevent the increase the range of a joint. For example, if the external fixator is used on a patients lower leg, an upper fixator ring (e.g., 106 in FIG. 1) may interfere with the motion of the patients knee. The use of the ring 200 instead of fixator ring 106 may prevent this limitation when an opening 205 in the ring 200 is aligned with the back of the patients lower leg. While a ⅝ ring 200 is shown in FIG. 2, other partial rings and U-shaped members may also be used in the external fixator to prevent such joint range limitations or for other reasons.

The ring may include a plurality of inner holes 210 and a plurality of tab holes 220. The inner holes 210 may be numbered from 210-1 to 21-40. As shown in FIG. 2 inner hole 210-1 is near the top center of the ring 200 and then the holes may be numbered along the right side of the ring to 210-19 as shown. The inner hole 210-20 then is adjacent to ring opening 205 and the holes are numbered along the left side of the ring to inner hole 21040 which is in the top center of the ring 200. In FIG. 2, nine tab holes 220-1 to 220-9 are illustrated. The tab holes 220 are situated on three tabs 222-1 to 222-3 as illustrated. The tabs 222 generally extend out from the ring 200 and provide a location for the struts (see 116 in FIG. 1) to be attached. The inner holes 210 generally provide locations where pins (see 110 in FIG. 1) or wires may be fixed to the ring 200. In some situations the struts may be attached to the inner holes 210, and the wires and pins may be attached to the tab holes 220. The inner holes 210 and the tab holes 220 may be any combination of threaded or unthreaded holes. Further, more or fewer inner holes 210, tab holes 220, or tabs 222 may be included in the ring 200. The number of holes distributed along the ring 200 provide many alternative locations to use to construct and affix the external fixator to the patient.

When wires (such at 112 in FIG. 1) are used to attach the ring 200 to the patient, the wire may be first placed through the patient's bone. A first end of the wire may be attached to inner hole 210-25 using a mounting member to fix the wire. Then a tensioner may be affixed to a second end of the wire, and the tensioner may apply tension to the wire which is then connected to inner hole 210-15 using another mounting member. Additional wires may be tensioned and affixed to the ring 200.

The tensioner may allow for a specific number of different discreet tensions to be applied to the wires, e.g., 50 kg, 100 kg, and 130 kg. In other situations the tension may be completely variable. Increased wire tension leads to more stable connections between the bone and the external fixator, so a significant amount of tension is often placed on the wires and hence the ring 200.

The attached tensioned wires may cause the ring 200 to deform. This ring deformation causes the locations of the various inner holes 210 and tab holes 220 to change from their normal location. With the tensions typically used on the wires, the tab holes near the ends 206, 207 of the ring, may be displaced by 10 mm to 20 mm or more. The system that generates the treatment plan based upon the external fixator configuration and images taken of the attached external fixator, assumes that the location of the holes in the rings are at known positions. Thus, the treatment plan is determined based upon the known configuration of the external fixator. Because of the use of the ⅝ ring and tensioned wires, the locations where the struts are attached to the rings may be 10 mm, 20 mm, or more different from the ideal locations. This causes errors in the treatment plan. In order to provide the most effective treatment plan, the accuracy of the locations of the holes in the plate may be less than 1 mm. Depending upon the precise application of the external fixator the desired accuracy may be more or less. Embodiments for correcting for these distortions in the ring will be describe below.

Figure 3:
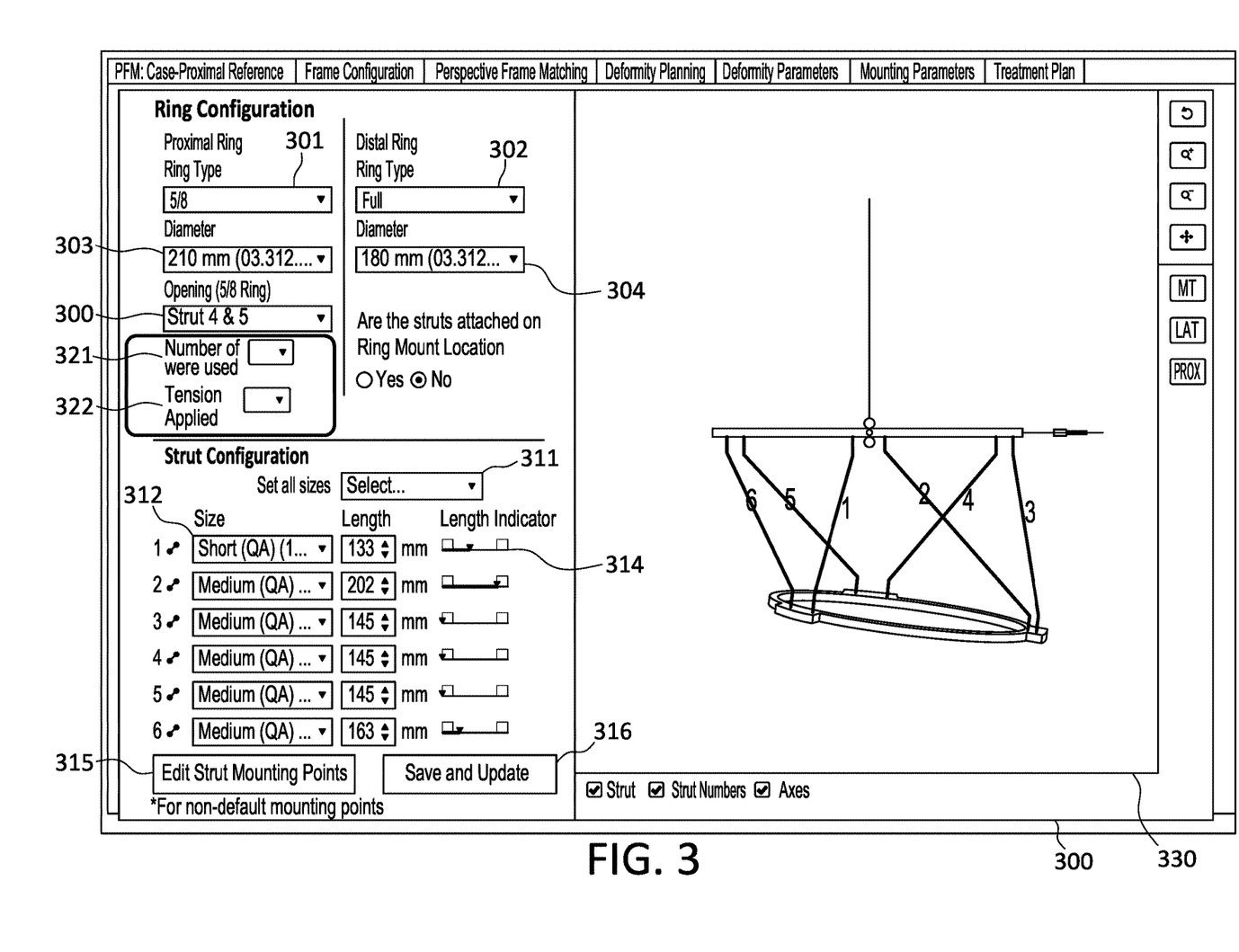
FIG. 3 illustrates a graphical user interface.

A first embodiment for correcting for ring distortion includes using lookup tables. Once the exterior fixator is in place the surgeon or user may input information regarding the configuration of the external fixator into a graphical user interface of the software tool used to generate the treatment plan. FIG. 3 illustrates such a graphical user interface 300. In some examples, the configuration information may include one or more geometric characteristics (e.g., size, length, diameter, etc.) of one or more elements of the fixation apparatus, such as struts, hinges, rings, and others. In some examples, the configuration information may include information such as ring types (e.g., full ring, foot plate, ⅝, etc.), indications of mounting points (e.g., ring holes) used for strut mounting, and other information. In some examples, the configuration information may also include information about marker elements, for example that are mounted to components of the fixation apparatus, such as struts, hinges, and rings. Referring now to FIG. 3, an example configuration information entry interface 300 is shown. As shown, interface 300 includes ring type indicators 301 and 302, which, in this example, are drop down menus that may be used to select ring types for the proximal and distal rings, respectively. Indicator 301 is set to "⅝" to indicate that the proximal ring is a ⅝ ring, and indicator 302 is set to the "Full" option to indicate that the distal ring is a full ring. Interface 300 also includes diameter indicators 303 and 304, which, in this example, are drop down menus that may be used to select diameters or lengths for the proximal and distal rings, respectively.

The interface 300 also includes controls for entry of strut information. In particular, interface 300 includes six drop down menus 312 that may each be used to indicate a size of a respective strut. A global strut size indicator 311 may also be used to globally select a size for all six struts. Length selectors 313 may be each be used to select a length of a respective strut. Length indicators 314 may be each be used to provide a visual representation of the lengths of the respective struts. It is noted that the length indicators 314 do not necessarily depict the actual exact length of each strut, but rather represent the comparative lengths of the struts with respect to one another.

In some examples, the treatment plan software may initially assume that each strut is mounted into standard mounting points (e.g., tab holes), which are commonly or typically used mounting points for a respective fixation apparatus. It is noted, however, that struts are not necessarily required to be mounted into standard mounting points. For example, in some cases, selecting Edit Strut Mounting Points button 315 may allow a user to select non-standard mounting points for one or more struts. For example, in some cases, selection of button 315 may cause display of a graphical representation of rings including representations of standard and non-standard mounting points on the rings. The user may then, for each strut, select a graphical representation of a standard or non-standard mounting point at which the strut is mounted.

A Save and Update button 316 may be selected to save and update the configuration information values shown in interface 300. In some examples, selection of button 316 may cause interface 300 to display and/or update a graphical representation 330 of the fixation apparatus generated based, at least in part, on the entered configuration information. The graphical representation 330 may be displayed using one or more graphical user interfaces of a computing system. The graphical representation 330 includes six struts that may be color-coded (not shown) in multiple colors for easy identification. For example, in some cases, each of the struts (or at least two of the struts) may be shown in different colors with respect to one another. The struts in graphical representation 330 may have sizes, lengths, mounting points, and other features corresponding to entered configuration information. Graphical representation 330 also depicts the fixator rings, which may have diameters/lengths, ring types, and other features corresponding to entered configuration information. Graphical representation 320 may, for example, improve efficiency and reliability by providing the user with a visual confirmation of information entered into interface 300, for example to allow fast and easy identification of errors or other problems.

Interface 300 may also include fields related to distortion compensation. In this example where the ⅝ ring is used additional fields Opening 320, Number of wires used 321, and Tension applied 322 are displayed. These fields may be displayed when rings are used that may require distortion compensation. Opening field 320 indicates between which struts the opening of the ⅝ ring is located (in this case struts 4 and 5). Opening field 320 may also be a drop down menu with pairs of adjacent struts listed for the user to select. In other embodiments two separate fields may be used, where each field indicates one of the struts adjacent to the ring opening. Instead of drop down menu(s), the Opening field may be a text box where the surgeon types in the struts adjacent the ring opening. Alternatively, when the user clicks the Opening Field menu 320, the struts may be entered by selecting the struts as illustrated in graphical representation 330.

The Number of wires used field 321 may also be a drop down menu that indicates how may wires are attached to the ⅝ ring. This instead may be a text box where the surgeon types in the number of wires attached to the ⅝ ring.

The Tension Applied field 322 may be a drop down menu that includes a list of discrete tension values. The surgeon selects the tension value used on the wires. A tensioning tool used to tension the wires may have settings for specific discrete tension values that align with the values in the drop down menu. In other embodiments the Tension Applied field 322 may be a text box where the surgeon types in the tension value used.

Table 1 illustrates the locations of the nine tab holes 220-1 to 220-9 (TH_1 to TH_9) of the ⅝ ring 200 in X, Y, and Z coordinates in mm. In FIG. 2 the X and Z axes are as shown with the positive Y axis extending up out of the page.

TABLE 1

| TAB HOLE COORDINATES | | | |
|---|---|---|---|
| Hole | X | Y | Z |
| TH-1 | −13.593 | 0.000 | 142.352 |
| TH-2 | 0.000 | 0.000 | 143.000 |
| TH-3 | 13.593 | 0.000 | 142.352 |
| TH-4 | 130.077 | 0.000 | −59.404 |
| TH-5 | 123.842 | 0.000 | −71.500 |
| TH-6 | 116.484 | 0.000 | −82.948 |
| TH-7 | −116.484 | 0.000 | −82.948 |
| TH-8 | −116.480 | 0.000 | −67.250 |
| TH-9 | −130.077 | 0.000 | −59.404 |

When one or more wires are attached to the ⅝ ring and tensioned, the tab hole locations of Table 1 are not accurate anymore. Table 2 illustrates the locations of the nine tab holes 220 for specific numbers of wires and specific tension values. In this case the table includes values for one, two, or three wires, and for tensions of 50 kg, 100 kg, and 130 kg. This leads to nine different wire and tension combinations. When the surgeon inputs the number of wires used and the tension value use, the updated locations of the tab holes from the lookup Table 2 are used to calculate a treatment plan. As a result the treatment plan will be more accurate and better achieve the desired treatment.

TABLE 2

| Deformation Lookup Table For 03.312.740 probed from model. | | | Number of Implants Tensioned | | |
|---|---|---|---|---|---|
| | | | 1 Wire | 2 Wire | 3 Wire |
| Force Applied | 50 kg | TH1 | X: −13.593, Y: 0.000, Z: 142.352 | X: −13.592, Y: 0.000, Z: 142.351 | X: −13.591, Y: 0.000, Z: 142.350 |
| | | TH2 | X: 0.000, Y: 0.000, Z: 143.000 | X: 0.000, Y: 0.000, Z: 143.000 | X: 0.000, Y: 0.000, Z: 143.000 |
| | | TH3 | X: 13.593, Y: 0.000, Z: 142.352 | X: 13.592, Y: 0.000, Z: 142.351 | X: 13.591, Y: 0.000, Z: 142.350 |
| | | TH4 | X: 129.000, Y: 0.000, Z: −59.600 | X: 127.000, Y0.000, Z: −59.800 | X: 125.000, Y: 0.000, Z: −60.000 |
| | | TH5 | X: 122.000, Y: 0.000, Z: −71.600 | X: 120.000, Y: 0.000, Z: −71.800 | X: 118.000, Y: 0.000, Z: −72.000 |
| | | TH6 | X: 115.000, Y: 0.000, Z: −83.000 | X: 113.000, Y: 0.000, Z: −83.500 | X: 111.000, Y: 0.000, Z: −84.000 |
| | | TH7 | X: −129.000, Y: 0.000, Z: −83.000 | X: −127.000, Y: 0.000, Z: −83.500 | X: −125.000, Y: 0.000, Z: −84.000 |
| | | TH8 | X: −122.000, Y: 0.000, Z: −71.600 | X: −120.000, Y: 0.000, Z: −71.800 | X: −118.000, Y: 0.000, Z: −72.000 |
| | | TH9 | X: −115.000, Y: 0.000, Z: −59.600 | X: −113.000, Y: 0.000, Z: −59.800 | X: −111.000, Y: 0.000, Z: −60.000 |
| | 100 kg | TH1 | X: −13.592, Y: 0.000, Z: 142.351 | X: −13.591, Y: 0.000, Z: 142.350 | X: −13.590, Y: 0.000, Z: 142.349 |
| | | TH2 | X: 0.000, Y: 0.000, Z: 143.000 | X: 0.000, Y: 0.000, Z: 143.000 | X: 0.000, Y: 0.000, Z: 143.000 |
| | | TH3 | X: 13.592, Y: 0.000, Z: 142.351 | X: 13.591, Y: 0.000, Z: 142.350 | X: 13.590, Y: 0.000, Z: 142.349 |
| | | TH4 | X: 127.000, Y: 0.000, Z: −59.800 | X: 125.000, Y: 0.000, Z: −60.000 | X: 124.000, Y: 0.000, Z: −60.200 |
| | | TH5 | X: 120.000, Y: 0.000, Z: −71.800 | X: 118.000, Y: 0.000, Z: −72.000 | X: 117.000, Y: 0.000, Z: −72.200 |
| | | TH6 | X: 113.000, Y: 0.000, Z: −83.500 | X: 111.000, Y: 0.000, Z: −84.000 | X: 110.000, Y: 0.000, Z: −84.300 |
| | | TH7 | X: −127.000, Y: 0.000, Z: −83.500 | X: −125.000, Y: 0.000, Z: −84.000 | X: −124.000, Y: 0.000, Z: −84.300 |
| | | TH8 | X: −120.000, Y: 0.000, Z: −71.800 | X: −118.000, Y: 0.000, Z: −72.000 | X: −117.000, Y: 0.000, Z: −72.200 |
| | | TH9 | X: −113.000, Y: 0.000, Z: −59.800 | X: −111.000, Y: 0.000, Z: −60.000 | X: −110.000, Y: 0.000, Z: −60.200 |
| | 130 kg | TH1 | X: −13.591, Y: 0.000, Z: 142.350 | X: −13.590, Y: 0.000, Z: 142.349 | X: −13.589, Y: 0.000, Z: 142.348 |
| | | TH2 | X: 0.000, Y: 0.000, Z: 143.000 | X: 0.000, Y: 0.000, Z: 143.000 | X: 0.000, Y: 0.000, Z: 143.000 |
| | | TH3 | X: 13.591, Y: 0.000, Z: 142.350 | X: 13.590, Y: 0.000, Z: 142.349 | X: 13.589, Y: 0.000, Z: 142.348 |
| | | TH4 | X: 125.000, Y: 0.000, Z: −60.000 | X: 124.000, Y: 0.000, Z: −60.200 | X: 123.000, Y: 0.000, Z: −60.400 |
| | | TH5 | X: 118.000, Y: 0.000, Z: −72.000 | X: 117.000, Y: 0.000, Z: −72.200 | X: 116.000, Y: 0.000, Z: −72.400 |
| | | TH6 | X: 111.000, Y: 0.000, Z: −84.000 | X: 110.000, Y: 0.000, Z: −84.300 | X: 109.000, Y: 0.000, Z: −84.600 |
| | | TH7 | X: −125.000, Y: 0.000, Z: −84.000 | X: −124.000, Y: 0.000, Z: −84.300 | X: −123.000, Y: 0.000, Z: −84.600 |
| | | TH8 | X: −118.000, Y: 0.000, Z: −72.000 | X: −117.000, Y: 0.000, Z: −72.200 | X: −116.000, Y: 0.000, Z: −72.400 |
| | | TH9 | X: −111.000, Y: 0.000, Z: −60.000 | X: −110.000, Y: 0.000, Z: −60.200 | X: −109.000, Y: 0.000, Z: −60.400 |

An inspection of the values of Table 2 shows that as the tension increases and as the number of wires increases, the hole displacement increases. This is especially true for tab holes 220-4 to 220-9 that are closer to the ring ends 206, 207. For example for table hole 220-6, the X coordinate is 116.484 mm. For the one wire case the X coordinate becomes 115 mm, 113 mm, and 111 mm for tensions of 50 kg, 100 kg, and 130 kg respectively. As can be seen, with increasing tension the amount of displacement of the hole from its normal position increases to 5.484 mm. In another example, for a tension of 130 kg the X coordinate becomes 111 mm, 110 mm, and 109 mm for one, two, and three wires respectively. In the example of table 2 displacements of up to 7 mm or more may be experienced by the tab holes 220. If such displacement errors are not compensated, then the treatment plan may not achieve the desired treatment or may require trial and error adjustments to the plan while treatment is ongoing. By using the lookup table to more accurately determine the locations of the tab holes, the treatment plan may be more accurately determined.

Figure 4:
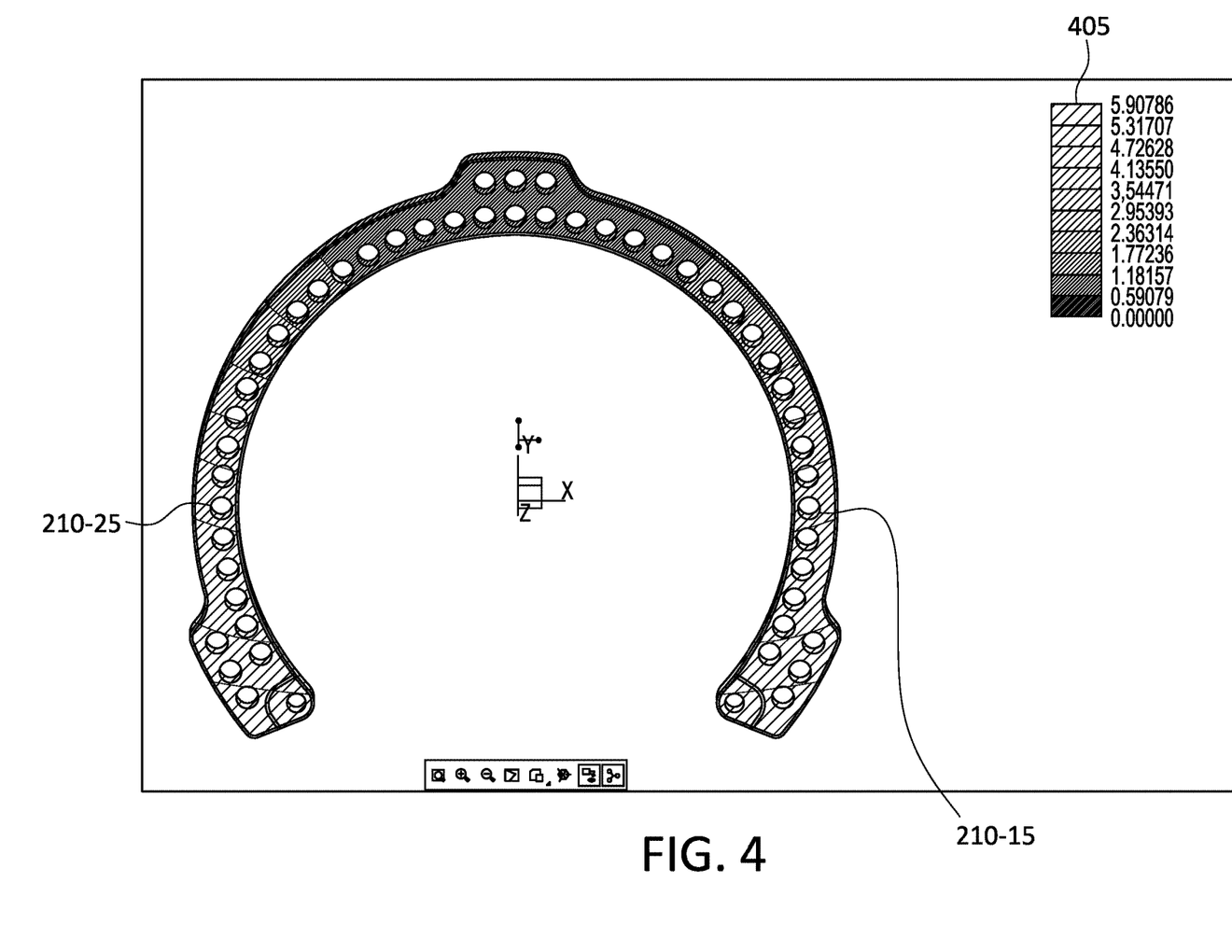
FIG. 4 illustrates the variation in hole displacement across the ring for a single wire with a tension of 130 kg.

FIG. 4 illustrates the variation in hole displacement across the ring for a single wire with a tension of 130 kg. In this example, the ring is modeled using finite element analysis (FEA) with one wire attached to inner holes 210-15 and 210-25 with a tension of 130 kg. The maximum displacement is approximately 5.9 mm, and the displacement values drop down to near zero for the holes near tab 222-1. Ten different displacement ranges are shown by the different colors/shadings as shown by the legend 405. Based upon this FEA, values may be determined for use in the displacement lookup Table 2. Each of the different scenarios may be analyzed and the hole displacement information generated.

It is noted that lookup Table 2 has some built in assumptions. The first is that the wires are assumed to be located at some nominal locations. Such locations may be selected to minimize the actual displacement error when the nominal locations are not used. Also, lookup Table 2 also assumes that the same tension is applied to each wire.

Lookup Table 2 may be expanded to include additional variations. First, additional variations may be developed for when two or more wires have different tensions. In this case the table would be expanded to be dependent upon the tensions placed on each of the wires. Such information may be captured by expanding the interface 300 to include separate Tension Applied fields for each wire.

Lookup Table 2 may be further expanded to include additional variations in the location of the wires. In such a case the interface 300 may be expanded to include input of the specific holes to which the wire(s) are connected. Additional lookup table entries may be generated that correspond to different wire locations. Because of the large number of holes (in this case there are 40 inner holes 210) the combinations may become very large. As the variations in displacement resulting for holes near one another is small, the holes may be, for example, grouped into groups of 5, and a wire attached to one of the holes is used to generate values that then will be used for each of the holes in the group. This may greatly reduce the number of different lookup table entries that need to be generated.

In yet another variation, if the tension value is not a discrete value, then the tables may be generated using a range of nominal values, and then the specific hole locations may be calculated by interpolating between the various nominal values. Various numerical methods may be used to generate these values. This same approach may be applied to refining the hole locations based upon the wires being attached to different holes. In such situations trend lines may be present and numerical methods may be used to calculate more specific hole location values.

As discussed above FEA may be used to generate the hole location information for the various different use cases. In other embodiments, actual rings may be tensioned with wires and hole locations determined.

The size of the lookup tables and the effort to generate the tables may be traded off with the needed accuracy of the updated hole information. Such a tradeoff may be driven by the treatment plan accuracy requirements versus table lookup size and the effort to generate the data. It may also be possible to implement a FEA capability in the treatment plan tool that is able to take in the specific configuration of the external fixator and calculate accurate hole locations to be used in determining the treatment plan. This would greatly increase the computing resources needed and the complexity of the software implementing the treatment plan tool, but it would provide increased accuracy of the hole locations, and hence treatment plan accuracy.

A second embodiment for correcting for ring distortion includes taking a post-operative physical measurement of the ring opening. That measurement of the opening may then be input into the interface 300 instead of receiving information about the number of wires and tension on those wires. Accordingly the interface 300 may include a field that allows for a user to enter the opening measurement value. This opening measurement value may then be used to calculate the new locations of the various holes after the ring has been tensioned and installed. Because as the size of the opening changes, the change in the location of the various holes will follow a well defined trendline. Accordingly, FEA may be used to characterize these trendlines as a function of the opening measurement. Alternatively, actual physical opening measurements may instead be taken on a ring that has been stressed to result in various opening values.

The opening measurement may be an input into an equation, which may be a linear or higher order equation, that models the change of the hole location as a function of opening size. Alternatively, a lookup table may be used that is indexed by the opening measurement. Depending upon the resolution of the lookup table, the hole locations may be further refined by using interpolation between two or more entries in the lookup table. This process may be done for two (if for example there is no variation in the Y dimension) or three dimensions. As before, the new hole locations are then used to generate the treatment plan.

The opening measurement may be accomplished using a ruler or a specially made tool that standardizes the opening measurement. The ring may have specific markers that are used to designate the specific points to use to make the opening measurement. Also X-ray tape may be used to help with the measurement as well. X-ray tape with a radiopaque scale could be used to display the measurement on the X-ray.

A third embodiment for correcting for ring distortion includes taking a post-operative digital measurement of the ring opening. One way is for the user to indicate specific predetermined features of the ring that are then used to determine the current measurement of the ring opening. The treatment plan software currently receives such input from the user, so this approach would be an extension of that requested input.

In another embodiment, two or more radiographic markers may be placed on the ring. The treatment plan software may then determine the coordinates of these radiographic markers and use their locations to determine current measurement of the ring opening.

Visual camera data may be used to help calculate the opening measurement to provide a scaling factor to measurements made based upon an X-ray of the external fixator. Once an opening measurement value is determined, then the new hole locations may be found in the same manner as discussed above with regard to the physical measurement of the ring opening.

A fourth embodiment for correcting ring distortion includes using a special drawing tool in planning software to trace the ring to strut angle as input to determine a new ring shape. The ring to strut angle measurement can be used in combination with other frame configuration parameters to estimate how deforming forces have reshaped the frame. This would be an iterative process where the user starts with best guess of bending and generates a two dimensional to three dimensional match. If the match is unsatisfactory, the user may improve the match by changing the amount of assumed deformation and iterating the process. If a good first match is obtained that is not perfect, a method could be implemented where the surgeon tests varying deformation via a scroll wheel type adjustment.

A fifth embodiment for correcting for ring distortion includes using in situ strain measurements. One or more strain gauges may be built into the ring. As the ring is deformed during construction and attachment of the external fixator, the stain gauge measures the strain in the ring. The location of the strain gauge is selected to provide the best relationship between measured stain and the change in the location of the holes in the ring.

FEA may be used to determine the relationship between the hole location and the strain. Like for the opening measurement above, the strain measurement may be fed into an equations that determines the location of the hole based upon the specific measured strain. The equations may be linear, non-linear, or higher order equations that model the variation of the hole as a function of the strain measurement. Likewise, lookup tables may be used to determine the hole locations and then interpolation using various table entries may further refine the accuracy of the hole location. Further, finite element models of the ring may be used along with the measured strain to determine the new locations of the holes.

The stain gauge may also be used to determine if wire tension is reduced or lost. Loss of wire tension may reduce the effectiveness of the treatment program. Also the loss of wire tension may help with infection detection and prevention.

The strain gauge may provide a visual read out that is read by the surgeon and then input into the visual interface 300 so that the treatment plan software may determine the new plate hole locations. Alternatively, the strain gauge may provide a digital output of the strain measurement. This may be communicated via wired or wireless connection to the computer hosting the treatment plan software.

If more than one strain gauge is used, each gauge may be associated with a specific set of holes, such that the change is location of the associated holes is based upon the measurement from the associated strain gauge. For example, two stain gauges may be used. One may be located on each side of the ring, e.g., a first strain gauge adjacent inner hole 210-10 and a second strain gauge adjacent inner hole 210-30. The first strain gauge may be used for the movement of tab holes 220-4, 220-5, and 220-6. The second strain gauge may be used for the movement of tab holes 220-7, 220-8, and 220-9. Either strain gauge (or even a third strain gauge) may be used for the movement of tab holes 220-1, 220-2, and 220-3.

A sixth embodiment for correcting for ring distortion may include using various sensing techniques for determining the new location of the holes. For example, visual images or lidar images may be taken of the ring in the installed external fixator. Various processing techniques may be used to identify specific holes or other features of the ring. For example, the location of holes adjacent to holes where the struts are connected may be used to determine the correct location of strut holes. In other situations, these sensors may be used to make an estimate of the ring opening and the same process as described above may be used to determine the new hole locations based upon the opening measurement.

Any of the embodiments above may be used to provide a more accurate estimate of the locations of the various holes in a ring in the external fixator. This determination would be made before the treatment plan is determined. Also this process may be used during the treatment plan to recalculate or update the treatment plan.

Figure 5:
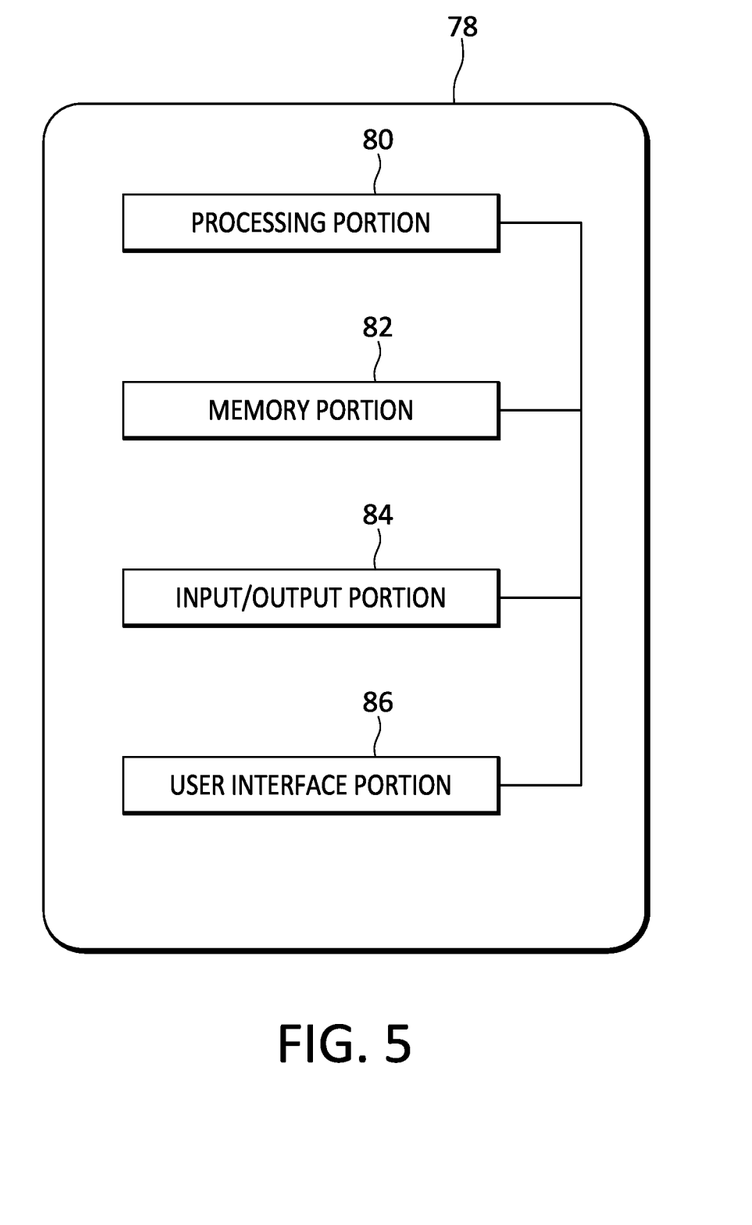
FIG. 5 illustrates a suitable computing device that may be configured to perform any or all of the fixation apparatus control, correction, and manipulation techniques set forth herein.

Referring to FIG. 5, a suitable computing device such as example computing device 78 may be configured to perform any or all of the fixation apparatus control, deformation correction, manipulation techniques, and treatment plan generation set forth above. It will be understood that the computing device 78 may include any appropriate device, examples of which include a desktop computing device, a server computing device, or a portable computing device, such as a laptop, tablet, or smart phone.

In an example configuration, the computing device 78 includes a processing portion 80, a memory portion 82, an input/output portion 84, and a user interface (UI) portion 86. It is emphasized that the block diagram depiction of the computing device 78 is exemplary and not intended to imply a specific implementation and/or configuration. The processing portion 80, memory portion 82, input/output portion 84, and user interface portion 86 may be coupled together to allow communications therebetween. As should be appreciated, any of the above components may be distributed across one or more separate devices and/or locations.

In various embodiments, the input/output portion 84 includes a receiver of the computing device 78, a transmitter of the computing device 78, or a combination thereof. The input/output portion 84 is capable of receiving and/or providing information pertaining to communicate a network such as, for example, the Internet. As should be appreciated, transmit and receive functionality may also be provided by one or more devices external to the computing device 78.

The processing portion 80 may include one or more processors. Depending upon the exact configuration and type of processor, the memory portion 82 may be volatile (such as some types of RAM), non-volatile (such as ROM, flash memory, etc.), or a combination thereof. The computing device 78 may include additional storage (e.g., removable storage and/or non-removable storage) including, but not limited to, tape, flash memory, smart cards, CD-ROM, digital versatile disks (DVD) or other optical storage, magnetic cassettes, magnetic tape, magnetic disk storage or other magnetic storage devices, universal serial bus (USB) compatible memory, or any other medium which may be used to store information and which may be accessed by the computing device 78.

The computing device 78 also may contain the user interface portion 86 allowing a user to communicate with the computing device 78. The user interface 86 may include inputs that provide the ability to control the computing device 78, via, for example, buttons, soft keys, a mouse, voice actuated controls, a touch screen, movement of the computing device 78, visual cues (e.g., moving a hand in front of a camera on the computing device 78), or the like. The user interface portion 86 may provide outputs, including visual information (e.g., via a display), audio information (e.g., via speaker), mechanically (e.g., via a vibrating mechanism), or a combination thereof. In various configurations, the user interface portion 86 may include a display, one or more graphical user interfaces, a touch screen, a keyboard, a mouse, an accelerometer, a motion detector, a speaker, a microphone, a camera, a tilt sensor, or any combination thereof. Thus, a computing system including, for example, one or more computing devices 78 may include a processor, a display coupled to the processor, and a memory in communication with the processor, one or more graphical user interfaces, and various other components. The memory may have stored therein instructions that, upon execution by the processor, cause the computer system to perform operations, such as the operations described above. As used herein, the term computing system may refer to a system that includes one or more computing devices 78. For instance, the computing system may include one or more server computing devices that communicate with one or more client computing devices.

While example embodiments of devices for executing the disclosed techniques are described herein, the underlying concepts may be applied to any computing device, processor, or system capable of communicating and presenting information as described herein. The various techniques described herein may be implemented in connection with hardware or software or, where appropriate, with a combination of both. Thus, the methods and apparatuses described herein may be implemented, or certain aspects or portions thereof, may take the form of program code (i.e., instructions) embodied in tangible non-transitory storage media, such as floppy diskettes, CD-ROMs, DVDs, Blu-ray disks, hard drives, or any other machine-readable storage medium (computer-readable storage medium), wherein, when the program code is loaded into and executed by a machine, such as a computer, the machine becomes an apparatus for performing the techniques described herein. In the case of program code execution on programmable computers, the computing device will generally include a processor, a storage medium readable by the processor (including volatile and non-volatile memory and/or storage elements), at least one input device, and at least one output device, for instance a display. The display may be configured to display visual information. The program(s) may be implemented in assembly or machine language, if desired. The language may be a compiled or interpreted language, and combined with hardware implementations.

The techniques described herein also may be practiced via communications embodied in the form of program code that is transmitted over some transmission medium, such as over electrical wiring or cabling, through fiber optics, or via any other form of transmission. When implemented on a general-purpose processor, the program code combines with the processor to provide a unique apparatus that operates to invoke the functionality described herein. Additionally, any storage techniques used in connection with the techniques described herein may invariably be a combination of hardware and software.

While the embodiments described above use an open ring, some of the embodiments may be applied to closed rings as well, as some closed rings may have holes that move enough from their static positions due to wire tension and other structural stresses to require correction of these locations in order to provide the best treatment plan.

While each of the embodiments are described above in terms of their structural arrangements, it should be appreciated that the invention also covers the associated methods of using the embodiments described above.

While the techniques described herein may be implemented and have been described in connection with the various embodiments of the various figures, it is to be understood that other similar embodiments may be used or modifications and additions may be made to the described embodiments without deviating therefrom. For example, it should be appreciated that the steps disclosed above may be performed in the order set forth above, or in any other order as desired. Further, one skilled in the art will recognize that the techniques described in the present application may apply to any environment. Therefore, the techniques described herein should not be limited to any single embodiment, but rather should be construed in breadth and scope in accordance with the appended claims.

What is claimed is:

1. A computer-implemented method for producing a treatment plan to control manipulation of a fixation apparatus including a first element and a second element and struts to correct an anatomical structure deformity of an anatomical structure having first and second anatomical structure segments, comprising:
   receiving configuration information associated with the fixation apparatus, the configuration information comprising one or more geometric characteristics of one or more elements of the fixation apparatus and element deformation information;
   receiving, by a computing system, images of the fixation apparatus and the first and the second anatomical structure segments attached thereto;
   determining, by the computing system, based on the configuration information and the received images, positions and orientations of the first and the second anatomical structure segments in three-dimensional space relative to the fixation apparatus;
   determining hole locations of the first element based upon the deformation information;
   determining, by the computing system, manipulations to the fixation apparatus for correction of the anatomical structure deformity, the manipulations comprising adjustments to the struts based upon the determined hole location of the first element; and
   providing, by the computing system, to one or more users, indications of the manipulations to the fixation apparatus.

2. The computer-implemented method of claim 1, wherein
   the deformation information includes a number of wires used and a tension on the wires, and
   determining the hole locations of the first element based upon the deformation information includes using a lookup table to determine hole locations of the first element based upon the number of wires and the tension.

3. The computer-implemented method of claim 2, wherein the deformation information includes a tension value for each of the number of wires.

4. The computer-implemented method of claim 3, wherein the deformation information includes attachment hole location information for each of the number of wires and wire fixation devices.

5. The computer-implemented method of claim 2, wherein determining the hole locations of the first element based upon the deformation information includes using lookup table tension values and using interpolation to determine the hole locations.

6. The computer-implemented method of claim 2, wherein the lookup table is generated using finite element analysis of the first element.

7. The computer-implemented method of claim 1, wherein
   the deformation information includes a measurement of an element opening in the first element, and
   determining the hole locations of the first element based upon the deformation information includes using a lookup table to determine hole locations of the first element based upon the element opening measurement.

8. The computer-implemented method of claim 7, wherein the lookup table is generated using finite element analysis of the first element.

9. The computer-implemented method of claim 7, wherein determining the hole locations of the first element based upon the deformation information includes using lookup table element opening values and using interpolation to determine the hole locations.

10. The computer-implemented method of claim 7, wherein the element opening measurement is determined using a physical measurement.

11. The computer-implemented method of claim 10, wherein the physical measurement is determined using a dedicated measurement tool.

12. The computer-implemented method of claim 7, wherein the element opening measurement is determined using a digital measurement.

13. The computer-implemented method of claim 12, further comprising detecting markers in the received images of the fixation apparatus and producing the digital measurement of the element opening based upon the detected markers.

14. The computer-implemented method of claim 1, wherein
the deformation information includes a measurement of an element opening in the first element, and
determining the hole locations of the first element based upon the deformation information includes using a hole location equation to determine hole locations of the first element based upon the element opening measurement.

15. The computer-implemented method of claim 14, wherein the hole location equation is generated using finite element analysis of the first element.

16. The computer-implemented method of claim 1, wherein
the deformation information includes a measurement of strain from a first strain gauge in the first element, and
determining the hole locations of the first element based upon the deformation information includes using a lookup table to determine hole locations of the first element based upon the strain measurement.

17. The computer-implemented method of claim 16, wherein the lookup table is generated using finite element analysis of the first element.

18. The computer-implemented method of claim 17, wherein determining the hole locations of the first element based upon the deformation information includes using lookup table strain values and using interpolation to determine the hole locations.

19. The computer-implemented method of claim 16, wherein
the deformation information includes a measurement of strain from the first strain gauge in the first element, and
determining the hole locations of the first element based upon the deformation information includes using a hole location equation to determine hole locations of the first element based upon the strain measurement.

20. The computer-implemented method of claim 19, wherein the hole location equation is generated using finite element analysis of the first element.

21. The computer-implemented method of claim 16, wherein
the deformation information includes a measurement of a first strain from the first strain gauge and a second strain from a second strain gauge in the first element, and
determining the hole locations of the first element based upon the deformation information based upon the first strain measurement and the second strain measurement.

22. The computer-implemented method of claim 1, wherein the configuration information is received from one or more graphical user interfaces.

* * * * *